United States Patent [19]

Beazley et al.

[11] 4,404,110

[45] Sep. 13, 1983

[54] OZONATION OF PETROLEUM FEEDSTOCKS

[75] Inventors: Phillip M. Beazley, Littleton; Frank L. Dormish, Denver, both of Colo.

[73] Assignee: Marathon Oil Company, Findlay, Ohio

[21] Appl. No.: 219,272

[22] Filed: Dec. 22, 1980

[51] Int. Cl.$^3$ .................... E21B 43/22; C07C 139/00; C07C 143/00

[52] U.S. Cl. .......................... 252/8.55 R; 260/504 R; 260/505 R

[58] Field of Search ............... 252/8.55 D; 260/504 R, 260/512 R, 513 T, 505 R

[56] References Cited

U.S. PATENT DOCUMENTS

| | | | |
|---|---|---|---|
| 2,842,588 | 7/1958 | Honeycutt | 260/504 |
| 2,851,483 | 9/1958 | Blumer et al. | 260/504 |
| 3,508,611 | 4/1970 | Davis et al. | 252/8.55 X |
| 3,926,757 | 12/1975 | Rosinger | 204/162 |
| 3,956,372 | 5/1976 | Coleman et al. | 260/505 |
| 3,997,451 | 12/1976 | Plummer et al. | 252/8.55 |
| 4,089,788 | 5/1978 | McCarthy | 252/8.55 |
| 4,148,821 | 4/1979 | Nussbaum et al. | 260/505 |

FOREIGN PATENT DOCUMENTS 971186 7/1975 Canada .............................. 252/8.55

*Primary Examiner*—Herbert B. Guynn
*Attorney, Agent, or Firm*—Jack L. Hummel

[57] ABSTRACT

A process for the sulfonation of a hydrocarbon feedstock, particularly one containing naphthenes, is improved by ozonating the hydrocarbon feedstock prior to sulfonation. The ozonation results in a greater conversion of the sulfur trioxide to sulfonate, a reduction in the salts, for example, sulfites, which are formed, a decrease in the amount of colored bodies and a more efficient extraction and separation of unreacted hydrocarbons from the sulfonated product. The process is especially applicable to petroleum feedstocks such as crude oil, topped crude oil, gas oil and mixtures thereof.

11 Claims, No Drawings

OZONATION OF PETROLEUM FEEDSTOCKS

DESCRIPTION

Technical Field

The process of the present invention relates to the sulfonation of petroleum feedstocks and more particularly to the ozonation of the petroleum feedstocks prior to their sulfonation.

Background Art

Prior Art Statement

U.S. Pat. No. 2,842,588 improves the properties of a petroleum sulfonate by contacting the sulfonate with an ozone containing gas until a carboxyl acidity equivalent to at least 0.05 cc. of 1 N sodium hydroxide per 100 ml. of a 0.5 weight percent solution of the sodium salts of the sulfonic acids has been produced. U.S. Pat. No. 2,851,483 purifies mahogany sulfonic acids by heating them to a temperature of at least 125° F. in the presence of a peroxidized organic solvent in order to bleach the mahogany sulfonic compounds. U.S. Pat. No. 4,089,788 oxidizes hydrocarbon polymer sulfonate surfactants with hydrogen peroxide in order to convert the sulfite to sulfate thereby preventing the formation of precipitates in the presence of calcium. U.S. Pat. No. 3,926,757 discloses initiating the sulfoxidation of straight chain aliphatic or cyclaliphatic compounds with radiation, ozone or peroxide in the presence of sulfur dioxide and oxygen.

Most of the prior art is concerned with treating already sulfonated feedstocks in order to improve their properties, for example, reducing their sulfite content. However, none of the prior art teaches or suggests the pretreatment with ozone of the feedstock to be sulfonated in order to increase the conversion of the feedstock to sulfonates and to decrease the oxidation of naphthenes contained in the feedstock. This pretreatment results in a more efficient conversion of sulfur trioxide to sulfonate, decreases the amount of sulfites and possibly sulfates formed during the process and decreases the colored bodies contained in the sulfonate. This latter result produces a better sulfonate for domestic use as the sulfonate is more aesthetically pleasing. The ozone pretreatment also allows for a more efficient extraction and separation between the unreacted hydrocarbon and the sulfonate product because the unreacted hydrocarbon phase contains less sulfonate than processes which do not pretreat the hydrocarbon feedstock prior to sulfonation.

Disclosure of the Invention

Sulfonation of a petroleum feedstock is improved by treating the feedstock with ozone prior to the sulfonation process. The ozonation treatment increases the conversion of sulfur trioxide to sulfonates and/or decreases the amount of salts, for example, sulfite, formed. In the absence of the ozone treatment, it is known that sulfur trioxide will react with naphthenes present in the petroleum feedstock to form sulfonates. However, the sulfonation of the naphthene causes a tremendous consumption of the sulfur trioxide and results in the formation of sulfites. Therefore, although the exact action or actions of the ozone on the petroleum feedstock is not known, it is thought that the ozone prevents the oxidation by sulfur trioxide of readily oxidized components of the feedstock, e.g., naphthenes, by converting the readily oxidized components to another form, e.g., a hydroxy naphthene, which consumes less sulfur trioxide. A hydroxy naphthene will react readily with one mole of sulfur trioxide to form an organic sulfate which has surfactant properties, whereas, one mole of naphthene will react with more than one mole of sulfur trioxide. The organic sulfate as a result of subsequent processing conditions, e.g., sulfonation, may revert to its hydroxy form which also has surfactant properties. The ozone may also be acting on other moieties contained in the petroleum feedstock, e.g., nitrogen moieties, which tend to consume sulfur trioxide.

When the sulfonate produced by the process of the present invention is used in the formation of micellar solutions used for supplemental oil recovery, the micellar solutions can tolerate a broader range of cosurfactant concentration and still maintain their stability. This increases the potential compatibility of the micellar solution with respect to a greater number of reservoirs and their fluids. Moreover, the fluid which is produced from an oil reservoir flooded with a flood containing the petroleum sulfonates of this invention more readily separates into oil and water phases and tends to have less oil solubilized in the water phase, making it easier to recover the oil from the produced fluid.

The process of the present invention is particularly useful in the production of crude oil and especially gas oil sulfonates. While such sulfonates produced by this invention are intended to find their primary use in oil recovery processes, they, or fractions thereof, are also useful in other known applications of sulfonates, such as flotation, cutting oils and insecticide carriers.

Preferred Modes For Carrying Out the Invention

The process of the present invention is applicable to any process for the sulfonation of hydrocarbons which contain compositions which are easily oxidized by sulfur trioxide, e.g., naphthenes. It is especially beneficial in the sulfonation of petroleum feedstocks, preferably those containing naphthenes. The term petroleum feedstocks as used herein includes whole crude oils, crude oils which have been "topped" to remove the lighter ends having boiling points below about 150° C. and preferably below about 315° C., gas oil feedstocks obtained from crude oils and mixtures of these petroleum feedstocks. The petroleum feedstocks may be pure hydrocarbons or may contain sulfur, oxygen and nitrogen moieties. Preferred crude oil and fractions thereof are those with aromatic portions having molecular weights in the range of from about 200 to about 1,000, preferably from about 300 to about 800 and more preferably from about 350 to about 500. The percent aromatics and olefins in the crude oil and fractions thereof is preferably from about 10 to about 95, more preferably from about 20 to about 80 and most preferably from about 20 to about 50 weight percent.

The term gas oil as used herein is that fraction of a crude oil which has a boiling point range of from about 205° C. to about 650° C., has an average molecular weight of from about 250 to about 700 and has an A/AP (aliphatic to aromatic proton) ratio of about 5 to about 50 moles per mole and wherein from about 20 to about 100 percent of the feedstock molecules contain aromatic portions with the A/AP ratio of the aromatic portion being from about 3 to about 20 moles per mole. A preferred gas oil has an average molecular weight of from about 300 to about 500 and more preferably from about 350 to about 450. It is preferred that the A/AP ratio of the gas oil be from about 10 to about 45 and more preferably from about 15 to about 40. The preferred aromatic content of the gas oil is from about 30 to about 80 percent and more preferably from about 40 to about 60 percent by weight and the preferred A/AP ratio of the aromatic portion of the gas oil is from about 4 to about 18 moles per mole. The term gas oil includes atmospheric, light and heavy vacuum gas oils.

The ozonation of the petroleum feedstock is conducted at a temperature which is as low as possible, but which is sufficient for the feedstock to be fluid enough to allow an interaction between the ozone and the feedstock. As the temperature is increased, and particularly when it is increased above about 60° C., there is a greater tendency for the ozone to form dicarboxylic acids and other oxidation products from the feedstock which, if excessive, destroy the desired properties of the ozonated feedstock for subsequent sulfonation. Thus, the temperature of the ozonation is generally conducted at a temperature of from about 0° C. to about 100° C. and preferably from about 15° C. to about 40° C.

Since pure ozone is highly reactive and potentially explosive, it is preferred that the ozone be diluted, for example, with oxygen or air. Generally, when ozone is made by coronal discharge in oxygen, the maximum ozone concentration is about 8 percent, and when made in the presence of air, the maximum ozone content is about 4 percent. Thus, diluted ozone, irrespective of its source, is used in an amount to supply from about 0.02 to about 2.0 and preferably from about 0.2 to about 1.0 kilograms of ozone per 100 kilograms of petroleum feedstock.

The pressure of the ozonation process is not narrowly critical as long as it is sufficient to allow the ozone to be contacted with the feedstock being treated, e.g., by bubbling the ozone through the feedstock. Generally, the ozonation process is conducted at about atmospheric pressure. The time period of the ozonation process is a function of the composition of the feedstock, temperature of the process, the treatment level of the ozone, the degree of dilution of the ozone and the size of the ozonation equipment. The ozonation should be conducted for a time period which is adequate to allow sufficient contact time between the ozone and the feedstock to improve the condition of the feedstock. Generally, a contact time between the ozone and the feedstock of about one minute to about thirty minutes is sufficient.

The sulfonation reactor conditions are not narrowly critical. The temperature will normally be in the range of from about 27° C. to about 120° C., preferaby from about 38° C. to about 93° C. and more preferably from about 55° C. to about 82° C. Pressures will range from about 0.01 to about 150, preferably from about 0.15 to about 75 and more preferably from about 0.2 to about 5 atmospheres. The reaction times will be from about 0.001 to about 3,600, preferably from about 0.01 to about 360 and more preferably from about 0.02 to about 60 seconds.

Sulfonation reactors which are conventionally utilized in the processes for the sulfonation of hydrocarbons including, for example, falling film, scraped surface and stirred tank reactors, may be used in the process of this invention. In those instances where a sulfur trioxide diluent is used, a back mixed tubular reactor is preferred, and the materials introduced into the tubular reactor should be in turbulent flow.

It is preferred that an anhydrous sulfur trioxide feed that is free of impurities, such as sulfuric acid, which can cause deleterious side reactions, be used. From about 5 to about 30, preferably from about 7 to about 20 more preferably from about 8 to about 15 kilograms of sulfur trioxide is fed into the sulfonation reactor per 100 kilograms of petroleum feedstock. The sulfur trioxide can either be a liquid or vaporized state, however, the vaporized state is preferred.

The sulfur trioxide can be diluted with liquid or gaseous low molecular weight aliphatics, sulfur dioxide, air, nitrogen or other inert gases. The ratio of the diluent to sulfur trioxide should be from 0 to about 20, more preferably from about 1 to about 10 and most preferably from about 2 to about 6 moles of diluent per mole of sulfur trioxide. The preferred diluent for the sulfur trioxide is a recycle of the light ends containing a mixture of sulfur dioxide and light hydrocarbons which are obtained from the sulfonation reactor by a one stage flash.

Additionally, a product diluent, such as ethylene dichloride, trichloroethylene, nitrobenzene, nitropropane, naphtha, aliphatic hydrocarbons including hexane and similar substantially inert polar solvents may be introduced into the reactor to dilute and/or dissolve the sulfonic acid in the unreacted hydrocarbons. Generally, the product diluent is used in a concentration of from about 0 to about 20 kilograms, preferably from about 1 to about 10 kilograms and more preferably from about 3 to about 8 kilograms per kilogram of sulfur trioxide. In addition to acting as a diluent for the product, the same diluent may also act as a diluent for the sulfur trioxide. However, when naphtha or another diluent containing naphthene type structures is used as a diluent in the sulfonation process, the diluent should be pretreated with ozone, utilizing conditions previously described, prior to its use in the sulfonation process.

The desirability of a specific diluent is dependent upon the reactivity of the petroleum feedstock being sulfonated. Highly viscous petroleum feedstocks, such as heavy vacuum gas oils, often require a product diluent in addition to a sulfur trioxide diluent, while less viscous crude oils and atmospheric gas oils can be sulfonated with or without a product diluent. A preferred sulfur trioxide diluent for less viscous crudes, for example, whole crude oil or atmospheric gas oil is recycled sulfonic acids from the sulfonation reactor which contain sulfur dioxide and light hydrocarbons. More viscous petroleum feedstocks, e.g., heavy vacuum gas oils, utilize the same sulfur trioxide diluent and preferred product diluents are ethylene dichloride and hexane. Except when the sulfur trioxide diluent or product diluent is a recycled sulfonic acid, it is preferred that the diluents be removed, e.g., by steam stripping, prior to the separation of any unreacted hydrocarbons from the sulfonated hydrocarbon. The reaction products are then fractionated as desired. When a diluent is a solvent for the sulfonated petroleum feedstock, it is necessary to remove these diluents.

The sulfonated product is extracted with a solvent in order to free the sulfonate product from any unreacted hydrocarbon. Examples of suitable extraction solvents include water, low molecular weight aliphatic alcohols, ketones, ethers and semipolar hydrocarbons, such as benzene and toluene. Preferably, the amount of salts and unreacted hydrocarbon in the final product are controlled by regulating the extraction solvent to reaction product ratio and the makeup of the extraction solvent.

Thus, from about 0.1 to about 3, preferably from about 0.3 to about 1.5 and more preferably from about 0.6 to about 1 kilograms of extraction solvent per kilogram of the acid sulfonate product mixture are used. It is preferred that the extraction solvent be water or an aqueous alcohol. When the extraction solvent is aqueous alcohol, it is preferred that it be aqueous ethyl or isopropyl alcohol. It is preferred that an aqueous ethanol solution contain from about 20 to about 60 percent by weight ethanol with a total amount of ethanol not exceeding about 55 to about 60 percent by weight. When an aqueous isopropyl alcohol solution is used, it preferably contains from about 50 to about 80 percent by weight isopropyl alcohol and more preferably from about 55 to about 75 percent by weight isopropyl alcohol.

Either two or three phases will result from the addition of the extraction solvent. From top to bottom, these include a raffinate phase consisting primarily of unreacted hydrocarbons, an extract phase containing most of the petroleum sulfonate product and, depending upon whether alcohol is used, a brine phase containing salts and water. The extraction solvent, if any, is separated from the raffinate and extract phases, for example, by stripping. If water is the extraction solvent, it will generally remain with the extract phase. The pretreatment of the petroleum feedstock with ozone prior to its sulfonation generally allows this extraction step to be accomplished more efficiently, because the raffinate phase contains less sulfonate than processes not utilizing an ozone pretreatment.

The extract phase is then neutralized with sufficient base, preferably a monovalent base, such as sodium hydroxide, potassium hydroxide or ammonium hydroxide to form a neutralized petroleum sulfonate. The order of the neutralization step is not critical. If desired, it can be accomplished prior to the extraction of the petroleum sulfonate from the unreacted hydrocarbons.

If the petroleum feedstock contains wax, the wax can be extracted by the addition of a suitable alkyl hydrocarbon, such as kerosene or naphtha, which is added to either the neutralized or unneutralized acidic sulfonate product. The technique for extraction and the amount of extractant are well known in the art. For example, the kerosene is added in an amount of from about 0.02 to about 3.0 kilograms per kilogram of sulfonate product.

The petroleum sulfonates produced from the ozonated feedstock of this invention are useful in the formulation of micellar dispersions comprised of hydrocarbon, water and petroleum sulfonate, which are utilized in oil recovery processes. Examples of such micellar dispersions include micellar flooding of subterranean reservoirs with systems of the type taught by H. J. Hill, Reisberg, and G. L. Stegemeier, *J. Pet. Tech.*, 186 (February 1973), wherein relatively dilute aqueous "solutions" of surfactant and/or cosurfactant are injected; the process of R. L. Reed, et al, U.S. Pat. No. 3,885,628 wherein a mulitiphase system is injected; and U.S. Pat. No. 3,082,822 to L. W. Holm, et al, wherein substantially small slugs of anhydrous soluble oils are alternately injected with small slugs of water or other aqueous media; U.S. Pat. No. 3,682,247 to Jones; U.S. Pat. No. 3,687,201 to Son, et al; U.S. Pat. No. 3,740,343 to Jones, et al; U.S. Pat. No. 3,956,372 to Coleman, et al; U.S. Pat. No. 3,964,548 to Schroeder, et al; U.S. Pat. No. 3,997,451 to Plummer, et al; and U.S. Pat. No. 4,013,125 to Plummer, et al. Petroleum sulfonates are also useful in other types of surfactant floods used in oil recovery processes.

EXAMPLE 1

A 400 gram sample of a heavy vacuum gas oil cut of Crawford County, Illinois crude oil was diluted with an equal volume (approximately 550 grams) of ethylene dichloride (EDC). The mixture of gas oil and EDC was then sulfonated at a temperature of 30° C. (±2° C.) with sulfur trioxide vapor which had been diluted with 9 parts of nitrogen gas to 1 part of sulfur trioxide. The resulting acid sulfonate mixture was then neutralized with ammonium hydroxide. The EDC was vacuum distilled from the neutralized sulfonate mixture. The sulfonate product was then extracted from this mixture with an extraction solvent of naphtha and a 50 percent aqueous ethanol solution. Thereafter, the extraction solvent was stripped from the extracted sulfonate product. Water was added back to the product for ease of handling the sample. The final sulfonate product contained 3.22 percent by weight of salt, 7.47 percent by weight of ammonium sulfonate and 63.21 percent by weight of water. Of the sulfur trioxide which was fed into the sulfonation reactor, 60.8 percent by weight was converted to petroleum sulfonates recovered in the product, 27.8 percent by weight was converted to inorganic sulfite and sulfate salts and 5.6 percent by weight was converted to sulfonates which were lost to the brine and the raffinate phases of the extraction process.

EXAMPLE 2

For comparison, another sample of the same gas oil used in Example 1, was ozonated prior to sulfonation. A 800 gram sample of the gas oil diluted with 1,100 grams of ethylene dichloride was sparged with a mixture of oxygen and ozone for 17 minutes at about 15 p.s.i.a. and an ambient temperature of about 22° C. A total of 3.14 grams of ozone were delivered and 2.8 gram of ozone were absorbed resulting in a 0.35 percent by weight ozone treatment of the gas oil. Thereafter, half of the ozonated gas oil was sulfonated under the same conditions recited in Example 1. The separation of the raffinate from the sulfonate product in the extraction step was faster and more effective than the separation of the sulfonate product in Example 1. The sulfonate product contained 2.6 percent by weight salt, mainly sulfate, 7.0 percent by weight ammonium sulfonate and 70.3 percent by weight water. Of the sulfur trioxide fed into the sulfonation reactor, 64.4 percent was converted to petroleum sulfonate, 22 percent by weight was converted to salt and about 0.64 percent by weight was converted to sulfonates which were lost to the brine and raffinate phases of the extraction process. The product also contained fewer colored bodies as compared to the sulfonate product of Example 1.

EXAMPLE 3

The gas oil sulfonate of Example 1 was formulated into a micellar solution and the ozonated gas oil sulfonate of Example 2 was formulated into four different micellar solutions. The compositions of the micellar solutions are given in Table 1. Micellar solutions A, B and C utilized water produced from the Tensleep area of South Oregon Basin, Wyoming having 7,150 total dissolved solids and micellar solutions D and E utilized softened Madison reservoir water also of the South Oregon Basin of Wyoming having 3,678 total dissolved solids.

Each of the micellar solutions was then used to flood six inch Berea cores. The initial porosity ($\phi$) and permeability (k) in millidarcys (md) are given in Table 2. Each of the cores was initially saturated with South Oregon Basin Tensleep crude oil (So). Thereafter, each of the cores was flooded with water and the oil remaining after that flood was measured (Sor$_i$). Each of the cores was then flooded with a 16.7 percent pore volume injection of a micellar solution. Each micellar solution coreflood utilized polymer mobility buffers comprising 20 percent pore volume of 3,000 ppm of Dow 700 (a polyacrylamide) in Madison soft water (MSW), forty percent pore volume of 2,000 ppm of Dow 700 in MSW, 20 percent pore volume of 1,000 ppm Dow 700 in MSW and 100 percent pore volume of MSW. The oil remaining after each flood (Sor$_c$) was calculated by difference. The change in the oil content of the core as a result of the micellar flood is given as $\Delta$Sor$_c$. The percentage oil recovery from each of the cores by each of the micellar solutions is given in Table 2.

TABLE 1

| Micellar Solution | Gas Oil Sulfonate | Sulfonate —SO$_3$NH$_4$ (% wt/wt) | Salt (% wt/wt) | H$_2$O (% wt/wt) | Cosurfactant Ethoxylated Alcohols** ml/100 gm |
| --- | --- | --- | --- | --- | --- |
| A | Ex. 1 | 1.5 | 1.62 | 80 | 2 ml/100 gms |
| B | Ex. 2 | 1.5 | 1.60* | 80 | 2 ml/100 gms |
| C | Ex. 2 | 1.5 | 1.10 | 80 | 2 ml/100 gms |
| D | Ex. 2 | 1.5 | 0.83 | 80 | 2 ml/100 gms |
| E | Ex. 2 | 1.5 | 1.01* | 80 | 2 ml/100 gms |

*0.5 gram (NH$_4$)SO$_4$ was added to Sample B and 0.18 gram MgSO$_4$ was added to Sample E so these two samples would contain comparable amounts of salt as compared to the other micellar solutions.
**Conoco's 610-50-4, a mixture of ethoxylated alcohols having 6, 8 and 10 carbon atoms.

TABLE 2

| Core Flood | 6 inch Core | | Micellar Solution | Core Oil Saturations | | | | Oil Recovery (%) |
| --- | --- | --- | --- | --- | --- | --- | --- | --- |
| | $\phi$ (%) | k (md) | | So | Sor$_i$ | Sor$_c$ | $\Delta$Sor$_c$ | |
| 1 | 20.7 | 248 | A | 67.3 | 44.3 | 14.2 | 30.0 | 67.9 |
| 2 | 20.5 | 289 | B | 70.6 | 46.9 | 15.2 | 31.7 | 67.6 |
| 3 | 20.5 | 344 | C | 71.8 | 47.0 | 16.5 | 30.5 | 65.0 |
| 4 | 20.9 | 272 | D | 69.4 | 46.6 | 14.8 | 31.8 | 68.3 |
| 5 | 20.5 | 303 | E | 72.0 | 45.4 | 15.1 | 30.3 | 66.7 |

What is claimed is:

1. A process for the sulfonation of a petroleum feedstock containing naphthenes and selected from the group consisting of crude oil, topped crude oil, gas oil and mixtures thereof, comprising steps of:
   (a) ozonating said petroleum feedstock with about 0.02 to about 2 kilograms of ozone per 100 kilograms of feedstock, at a temperature of about 0° C. to about 100° C. and for a contact time sufficient to prevent excessive oxidation of the resulting ozonated feedstock; and
   (b) sulfonating said ozonated feedstock with sulfur trioxide under conditions sufficient to sulfonate said ozonated feedstock without excessive oxidation of said ozonated feedstock.

2. The process of claim 1 wherein the ozonation process is conducted at about atmospheric pressure.

3. A process for the sulfonation of a petroleum feedstock containing naphthenes and selected from the group consisting of crude oil, topped crude oil, gas oil and mixtures thereof, comprising the steps of:
   (a) ozonating said petroleum feedstock with about 0.02 to about 2 kilograms per 100 kilograms of petroleum feedstock, at a temperature of about 0° C. to about 100° C. for a contact time sufficient to prevent excessive oxidation of the resulting ozonated petroleum feedstock; and
   (b) sulfonating the ozonated feedstock with sulfur trioxide at a temperature of about 27° C. to about 120° C. and a pressure of about 0.01 to about 150 atmospheres with about 5 to about 30 kilograms of sulfur trioxide per 100 kilograms of ozonated feedstock.

4. The process of claim 3 wherein the ozonation is conducted at a temperature of from about 15° C. to about 40° C. with from about 0.2 to about 1 kilogram of ozone per 100 kilograms of petroleum feedstock.

5. The process of claim 1 or claim 4 wherein the petroleum feedstock is a gas oil having a boiling point of from about 205° C. to about 650° C., an average molecular weight of from about 250 to about 700, with an aliphatic to aromatic proton ratio of about 5 to about 50 moles per mole, wherein from about 20 to about 100 weight percent of the feedstock molecules contain aromatic portions and wherein the aliphatic to aromatic proton ratio of the aromatic portion is from about 3 to about 20 moles per mole.

6. The process of claim 5 wherein the gas oil has an average molecular weight of from about 300 to about 500 with an aliphatic to aromatic proton ratio of from about 10 to about 40 moles per mole, wherein from about 30 to about 80 weight percent of the feedstock molecules contain aromatic portions and wherein the aliphatic to aromatic proton ratio of the aromatic portion is from about 4 to about 18 moles per mole.

7. The process of claim 1 or claim 4 wherein the petroleum feedstock is selected from the group consisting of a crude oil and topped crude oil containing from about 10 to about 95 weight percent aromatics and having a molecular weight of from about 200 to about 1000 and wherein the topped crude oil has had light ends having boiling points below about 150° C. removed.

8. The process of claim 7 wherein the crude oil and topped crude oil contain from about 20 to about 80 weight percent aromatics and have a molecular weight of from about 300 to about 500 and wherein the topped crude oil has had light ends having boiling points below about 315° C. removed.

9. The process of claim 1 or claim 4 wherein the crude oil and topped crude oil contain from about 20 to about 50 weight percent aromatics and have a molecular weight of from about 350 to about 500, wherein the topped crude oil has been topped to remove lighter ends having boiling points less than about 315° C. and wherein the gas oil has a boiling point of from about 205° C. to about 650° C., an average molecular weight of from about 350 to about 450, an aliphatic to aromatic proton ratio of from about 15 to about 40 moles per mole and contains from about 40 to 60 weight percent aromatics which aromatic portion has an aliphatic to aromatic proton ratio of from about 4 to about 18 moles per mole.

10. A process for the recovery of oil from a subterranean formation comprising injecting a micellar dispersion comprising hydrocarbon, water and petroleum sulfonate into the subterranean formation, wherein the petroleum sulfonate is obtained by ozonating a petroleum feedstock selected from the group consisting of crude oil, topped crude oil, gas oil and mixtures thereof at a temperature of from about 15° C. to about 40° C. and at about atmospheric pressure in the presence of from about 0.2 to about 1.0 kilograms of ozone per 100 kilograms of petroleum feedstock for a time which is sufficient to cause the ozonation of the feedstock without causing excessive oxidation of the feedstock, thereafter sulfonating the ozonated petroleum feedstock with sulfur trioxide in an amount of from about 7 to about 20 kilograms of sulfur trioxide per 100 kilograms of ozonated petroleum feedstock at a temperature of from about 38° C. to about 93° C. and a pressure of from about 0.15 to about 75 atmospheres, and recovering from the subterranean formation the oil produced from the injection of the micellar dispersion.

11. The process of claim 10 wherein the petroleum feedstock is a gas oil.

* * * * *